United States Patent [19]

Helting

[11] 4,029,765

[45] June 14, 1977

[54] DERIVATIVES OF THE TETANUS TOXIN, PROCESS FOR THEIR PREPARATION AND AGENTS CONTAINING THEM

[75] Inventor: Torsten Bertil Helting, Marbach-Marburg an der Lahn, Germany

[73] Assignee: Behringwerke Aktiengesellschaft, Marburg an der Lahn, Germany

[22] Filed: Dec. 2, 1975

[21] Appl. No.: 637,028

[30] Foreign Application Priority Data

Dec. 3, 1974 Germany .................... 2457047

[52] U.S. Cl. .................. 424/92; 260/112 R
[51] Int. Cl.² .................... A61K 39/02
[58] Field of Search ............ 424/92; 260/112 R

[56] References Cited

UNITED STATES PATENTS 3,542,920  11/1970  Schwick et al. .................... 424/92
3,903,262  9/1975  Pappenhagen et al. ... 260/112 R X

OTHER PUBLICATIONS

Azuma et al., Chemical Abstracts, vol. 78, 39687q, (1973).

*Primary Examiner*—Dolph H. Torrence
*Attorney, Agent, or Firm*—Curtis, Morris & Safford

[57] ABSTRACT

The present invention relates to derivatives of tetanus toxin, a process for their preparation by treating an aqueous solution of tetanus toxin with an aliphatic mono- or dialdehyde, reacting the toxin, before or after the aldehyde treatment, with a denaturing agent in the presence of a compound reducing disulfide bridges obtaining the derivative of the light chain in the presence of the denaturing agent by way of protein-chemical isolation processes and suitably separating it from the denaturing agent, and compositions containing said derivatives.

18 Claims, No Drawings

DERIVATIVES OF THE TETANUS TOXIN, PROCESS FOR THEIR PREPARATION AND AGENTS CONTAINING THEM

The present invention relates to derivatives of tetanus toxin, a process for their preparation and agents containing them.

More particularly the present invention provides derivatives of tetanus toxin, a process for preparing them by modifying a partial molecule of the tetanus toxin and agents, in particular tetanus vaccines, which contain one of the derivatives of tetanus toxin.

The common tetanus vaccines for active immunization contain almost exclusively an antigen which has been prepared by the inactivation of tetanus toxin with formaldehyde. This substance called toxoid is provided with a large number of antigenic determinants, only a few of which are important, however, for the production of antibodies that protect against tetanus. The elimination of those determinants which are not required for protection is desirable, in order to obtain antigenic and/or immunogenic substances, of which — due to a narrower spectrum of determinant groups — an increased specificity and an improved compatibility may be expected.

Tetanus toxin is synthesized from cells of Cl. tetani and can be obtained from the cell mass as well as from the culture filtrate. Whereas the toxin obtained in an extracellular way consists of two polypeptide chains which may be separated after having been treated with agents reducing disulfide bridges (for example, dithiothreitol (DTT), dithioerythritol (DTE), mercaptoethanol, cysteine), under denaturing conditions, the intracellular toxin consists of a single polypeptide chain which can be converted in known manner, by a mild trypsin treatment, into a product which is identical to the extracellular toxin. The two fragments to be obtained of this product, which have been called, in this context, "light chain" (molecular weight of about 50,000) and "heavy chain" (molecular weight of about 100,000), could only be separated, up to now, by measures which are carried out under denaturing conditions, for example, in a solution containing sodium dodecyl sulfate, and the separated fragments can be kept in solution, according to the prior art, only by denaturing agents.

It was therefore the task of the present invention to modify the light chain of tetanus toxin in a way that it could be kept in a physiologically tolerable medium without losing its antigenicity. The light chain was to be available in particular as an essential immunogenic constituent of tetanus vaccines and was to replace the common toxoid in these substances.

It has now been found that this task can be solved by subjecting the light chain, either before or after the separation of the heavy chain from the molecular structure of tetanus toxin, which represents a complex of the light and heavy chains, to a slight chemical modification. By this method, the spontaneous irreversible precipitation of the light chain, which is otherwise observed after the elimination of denaturing agents like urea, can be avoided.

The present invention provides a process for the preparation of a derivative of the light chain of tetanus toxin, which comprises treating an aqueous solution of extracellular tetanus toxin with an aliphatic mono- or dialdehyde having a chain length of from 1 to 6 carbon atoms in an aldehyde concentration of from 0.01 to 0.05 molar of aldehyde at a temperature of from 1° to 20° C. for 5 minutes to 50 hours, reacting the toxin, before or after the aldehyde treatment, with a denaturing agent in the presence of a compound reducing disulfide bridges, subsequently obtaining the derivative of the light chain in the presence of the denaturing agent by way of protein-chemical isolation processes and suitably separating it from the denaturing agent.

A preferred variant of the process provides treating an aqueous solution of the tetanus toxin with an aliphatic mono- or dialdehyde having a chain length of from 1 to 6 carbon atoms, preferably formaldehyde, with an aldehyde concentration of from 0.02 molar to 0.03 mole, at a temperature of from 1° to 6° C for 2 to 20 hours, mixing the solution containing the toxin thus modified with an agent reducing disulfide bridges, obtaining the derivative of the light chain from the solution obtained in the presence of a denaturing agent by way of protein-chemical isolation processes and suitably separating it from the denaturing agent.

After the isolation of the derivative of the light chain of the tetanus toxin, the denaturing agent can be eliminated by way of dialysis or other comparable methods which allow the separation of low-molecular weight substances from high-molecular weight protein, for example by gel chromatography. The aldehyde, too, which has been used for the reaction but has not been used up, may be eliminated from the reaction mixtures by the same measures.

The derivative prepared according to the process of the invention no longer shows, after this treatment, the denaturing and precipitating properties of the light chain, in physiologically tolerable, isotonically aqueous media. The derivative no longer has the toxic property of tetanus toxin. It shows an antigen behavior and is in a position to induce antibodies protecting against tetanus in the human or animal organism.

The derivative prepared according to the invention is to be further purified by the common protein-chemical methods. In view of the admittedly high toxicity of native tetanus toxin and the fact — which is also known — that methods used for the dissociation of proteins only in the rarest cases lead to a 100 percent separation of accompanying substances, in particular of proteins having a similar structure, it is advantageous, however, to submit the product prepared according to the invention to a further aldehyde treatment, which comprises mixing the derivative of the light chain of the tetanus toxin with an aliphatic mono- or dialdehyde having a chain length of from 1 to 6 carbon atoms, preferably formaldehyde, up to an aldehyde concentration in the range of from 0.05 to 0.2 molar, preferably from 0.08 to 0.15 molar, and allowing it to stand for 14 to 28 days at a temperature in the range of from 20° to 37° C, eliminating the aldehyde, for example by way of dialysis, and obtaining the modified derivative of the light chain of the tetanus toxin.

The additional aldehyde treatment leads to a further stabilization of the light chain of the tetanus toxin and to the elimination of the residual toxicity which may still be present.

It is obvious that a stable derivative of the light chain may also be prepared by treating native tetanus toxin obtained from culture filtrates of Cl. tetani with substances reducing disulfide bridges, for example thiol compounds, by effecting the separation of the light chain from the heavy chain under denaturing conditions, preferably by way of chromatography in buffer solutions containing, for example, urea, subsequently by measures which allow the separation of low-molecular weight substances from high-molecular weight protein, by eliminating the denaturing agent suitably by gel chromatography, and by allowing the light chain to stand immediately with an aliphatic mono- or dialdehyde having a chain length of from 1 to 6 carbon atoms, preferably formaldehyde, with an aldehyde concentration of from 0.01 to 0.05 molar, for 5 minutes to 50 hours, at a temperature of from 1° to 20° C. A second aldehyde treatment in order to modify the derivative may optionally be performed. It is also possible, however, to react the light chain immediately after its isolation with the higher amount of aldehyde used for the modification of the derivative. However, these processes do not involve any advantage, since the yield of the derivative of the light chain prepared according to the latter process is considerably smaller than the one obtained according to the former process.

As starting material, use is made of tetanus toxin which has been obtained from culture filtrates of Cl. tetani in known manner (extracellular toxin). As an alternative there may be used a tetanus toxin prepared according to known processes which was obtained by extracting the Cl. tetani bacteria (intercellular toxin). In this case, however, a trypsin treatment to be carried out according to a known method is required before or after the reaction with aldehyde. If the light chain is not to be reacted with the aldehyde until after the separation from the heavy chain, it is clear that a trypsin treatment is to effected, in the case of intracellular toxin, before the reaction with aldehyde, as the proteolytic step represents a pre-requisite for the isolation of the light chain from this starting material. The tetanus toxin solution used as starting material contains the toxin suitably in a concentration of from 0.5 to 10 mg/ml.

As compounds reducing disulfide bridges, preference is given to thiol compounds. For this purpose there may be mentioned, for example, cysteine, mercapto-ethanol or dithioerythritol, preferably however, dithiothreitol. These compounds are added in amounts which cause a concentration of the compounds reducing disulfide bridges in the reaction mixture of from 0.05 to 0.3 molar.

By denaturing agents in the sense of the present process there are to be understood chemical compounds which help to dissociate protein molecules to obtain sub-units, in particular by dissolving hydrogen bonds. Known agents to dissolve hydrogen bonds are, for example, urea or guanidine hydrochloride. Urea has proved to be effective preferably in a concentration of from 4 to 6 molar, whereas guanidine hydrochloride is particularly effective in a concentration of from 2 to 4 molar.

It is not possible to isolate a modified light chain from the conventional tetanus toxoid, since in this case the use of considerably higher amounts of formaldehyde has resulted in a covalent cross-linking between the light and the heavy chains. However, there is no reason not to react any solution containng the light chain which has not been denatured, with aldehydes, in order to obtain derivatives having the advantageous properties with regard to stability and to antigenicity.

Besides the above-mentioned process variants, derivatives of tetanus toxin are also a subject of this invention, which are to be characterized by parameters resulting from their preparation according to the present process.

Finally, the present invention provides agents containing the tetanus toxin derivatives of the invention, in particular tetanus vaccines for prophylaxis against tetanus or for the preparation of tetanus antisera to be used for therapeutical or diagnostic purposes, but also diagnostic preparations containing the tetanus toxin derivatives or antisera obtained from them. In order to increase the solution stability of the product prepared according to the invention, it may be advantageous to add compounds used for the stabilization of protein solutions, such as amino acids or carbohydrates, to the physiologically tolerable aqueous medium in which the above product is dissolved.

It is recommended, for protection against microbial comtamination, to add antimicrobial substances, such as sodium timerfonate, to the solutions which are ready for use. For the preparation of a polyvalent vaccine, the tetanus toxin derivatives may be mixed with other antigens and/or toxoids in known manner.

The suitability of the products as vaccines has been proved in the following by tests which certify a good potency of the product.

POTENCY TEST a. In vitro

In order to determine the protective potency of the determinant groups which are present on the light chain, the following test was carried out:

A tetanus antitoxin serum of equine origin was absorbed with increasing amounts of the product according to Example 1. By way of examining the supernatants with the aid of the immunological double diffusion technique, the equivalence zone, in which the entire antibodies directed against the derivative of the light chain were precipitated, was determined. The evaluation of the antibodies in the animal test showed that up to 40% of the protecting antibodies from the antiserum of the product of the invention could be absorbed.

b. In vivo

Groups of 10 Guinea pigs each were given subcutaneously 1 ml (20 μg) of a suspension of the product prepared according to Example 1, adsorbed on 0.2% Al(OH)$_3$ gel. After 4 weeks, the animals were poisoned with tetanus toxin, corresponding to 100 minimum lethal doses (dlm = dosis letalis minima). All of the animals survived the poisoning.

2 Rabbits were immunized twice in an interval of 14 days with the product of the invention according to Example 3 (160 μg of tetanus toxin derivative suspended in 1 ml of complete Freund's adjuvant per application and animal). Three days after the second injection, blood tests were performed. The evaluation of the tetanus antitoxin titers in the serum was 100 IU/ml and/or 50 IU/ml. The following Examples serve to illustrate the invention.

EXAMPLE 1:

Tetanus toxin obtained from the culture filtate of Cl. tetani (40,000 floculation units (= LF units) corresponding to about 100 mg of protein) was dissolved in 100 ml of 0.1 molar phosphate buffer having a pH of 7.8 and was mixed with formaldehyde up to a final concentration of 0.03 mole of aldehyde; the solution was then allowed to stand for 16 hours at 4° C. Subsequently the solution was dialyzed against isotonic phosphate-buffered sodium hydroxide solution (PBS) having a pH value of 7.4, was concentrated to about 20 ml, and 150 mg of dithiothreitol and urea were added up to a final concentration of 6 moles/l. After having stood for 30 minutes at room temperature, the solution was introduced into a column (4.5 × 100 cm) of Sephadex$^{(R)}$ —G 150), which was equilibrated with 6 moles of urea in 0.1 molar trishydroxymethylaminomethane-HCl buffer (Tris) having a pH value of 8.0, and with an addition of dithiothreitol of 0.001 mole. The elution was performed with the equilibration mixture. Upon chromatography, two protein peaks were found by measuring the UV absorption at 280 nm. The material which corresponded to the first peak was discarded. The second peak contained the derivative of the light chain of the tetanus toxin. The solution of the isolated derivative of the light chain was dialyzed against 0.1 molar phosphate buffer and was mixed, in a protein concentration of 100 μg of protein/ml, with formaldehyde up to a final concentration of 0.1 molar of aldehyde and was then allowed to stand for three weeks at room temperature. After a final dialysis against 0.15 molar NaCl in order to eliminate the free formaldehyde, the modified derivative of the light chain was obtained. After concentration on an ultrafilter it could be processed into a vaccine in known manner. In this process, glycine or lysine could be used as stabilizers. As an adjuvant, use was made of a suspension of Al(OH)$_3$. Instead of formaldehyde, there could also be used — calculated on the molar aldehyde amount — glutardialdehyde, propionaldehyde or butyraldehyde, either in both steps or only in one step.

EXAMPLE 2

Tetanus toxin from cell extracts was mixed in a protein concentration of 0.1% in 0.1 molar phosphate buffer having a pH value of 7.8, with 100 μg of trypsin and was allowed to stand for 60 minutes at room temperature. Subsequently trypsin inhibitor obtained from bovine lungs (150 μg) was added, and the product was reacted according to Example 1 with formaldehyde, was dialyzed, reduced with dithiothreitol and subjectd to chromatography in urea solution.

EXAMPLE 3

Tetanus toxin (20 ml, 0.5% protein) in 0.1 molar Tris having a pH value of 8.0 was reacted with dithioerythrite (150 mg) and guanidine hydrochloride up to a final concentration of 4 moles/l, and was then subjected to chromatography in a manner analogous to that of Example 1. The second peak was pooled, the volume was adjusted to 400 ml, and the guanidine hydrochloride was eluted, together with the low-molecular weight components of the reaction mixture, by way of chromatography on a column with Sephadex$^{(R)}$—G 25 (column contents 2000 ml) with 0.1 molar phosphate buffer having a pH value of 7.8. The light chain was then mixed with formaldehyde up to a final concentration of 0.1 molar aldehyde and was allowed to stand for 3 weeks at room temperature. The processing into a vaccine was effected according to Example 1.

I claim:

1. A method for mixing a derivative of the light chain of tetanus toxin, which comprises treating an aqueous solution of extracellular tetanus toxin with an aliphatic mono- or di-aldehyde having 1 to 6 carbon atoms at an aldehyde concentration from 0.01 to 0.05 molar at a temperature from 1° C. to 20° C. for 5 minutes to 50 hours, reacting the toxin, before or after the aldehyde treatment, with a denaturing agent in the presence of a compound reducing disulfide bridges, subsequently isolating said derivative in the presence of the denaturing agent by protein-chemical isolation processes, and then separating said derivative from the denaturing agent.

2. A method as in claim 1 wherein the tetanus toxin used has been pretreated with trypsin.

3. A method as in claim 1 wherein the aldehyde is formaldehyde.

4. A method as in claim 1 wherein said denaturing agent is urea.

5. A method for making a modified derivative of the light chain of tetanus toxin, which comprises mixing the derivative of the light chain of tetanus toxin prepared by the method of claim 1 with an aliphatic mono- or dialdehyde having 1 to 6 carbon atoms, at an aldehyde concentration up to from 0.05 molar to 0.2 molar, allowing the mixture to stand for 14 days to 28 days at a temperature from 20° C to 37° C., and then removing the aldehyde to obtain said modified derivative.

6. A method as in claim 5 wherein the aldehyde is formaldehyde.

7. A method for making a derivative of the light chain of tetanus toxin, which comprises mixing the light chain of tetanus toxin, in the absence of a denaturing agent, with an aliphatic mono- or di-aldehyde having 1 to 6 carbon atoms, at an aldehyde concentration up to from 0.01 molar to 0.05 molar, allowing the mixture to stand from 5 minutes to 50 hours at a temperature from 1° C. to 20° C., and then removing the aldehyde to obtain said derivative.

8. A method as in claim 7 wherein the aldehyde is formaldehyde.

9. A method for making a modified derivative of the eight chain of tetanus toxin, which comprises mixing the light chain of tetanus toxin, in the absence of a denaturing agent, with an aliphatic mono- or di-aldehyde, at an aldehyde concentration up to from 0.05 molar to 0.2 molar, allowing the mixture to stand for 14 days to 28 days at a temperature from 20° C. to 37° C., and then removing the aldehyde to obtain said modified derivative.

10. A method as in claim 9 wherein the aldehyde is formaldehyde.

11. A derivative of the light chain of tetanus toxin obtained by the method of claim 1.

12. A modified derivative of the light chain of tetanus toxin obtained by the method of claim 5.

13. A modified derivative of the light chain of tetanus toxin obtained by the method of claim 7.

14. A modified derivative of the light chain of tetanus toxin obtained by the method of claim 9.

15. A tetanus vaccine containing a derivative of the light chain of tetanus toxin as defined in claim 11.

16. A tetanus vaccine containing a modified derivative of the light chain of tetanus toxin as defined in claim 12.

17. A tetanus vaccine containing a modified derivative of the light chain of tetanus toxin as defined in claim 13.

18. A tetanus vaccine containing a modified derivative of the light chain of tetanus toxin as defined in claim 14.